United States Patent [19]
Akiba et al.

[11] Patent Number: 5,225,276
[45] Date of Patent: Jul. 6, 1993

[54] FILTER AID FOR ANALYTICAL USE AND METHOD FOR PREPARING THE SAME

[75] Inventors: Masanori Akiba; Masahiro Kida; Shoichi Hamada, all of Okayama, Japan

[73] Assignee: Kabushiki Kaisha Hayashibara Seibutsu Kagaku Kenkyujo, Okayama, Japan

[21] Appl. No.: 800,893

[22] Filed: Oct. 25, 1991

Related U.S. Application Data

[63] Continuation of Ser. No. 248,282, Sep. 22, 1988, abandoned.

[30] Foreign Application Priority Data

Sep. 26, 1987 [JP] Japan ................... 62-242293

[51] Int. Cl.$^5$ .................................. D02G 3/00
[52] U.S. Cl. ............................ 428/359; 428/367; 428/360; 428/401; 428/402; 210/496; 210/503; 210/505; 210/510.1; 501/95
[58] Field of Search ............... 428/401, 364, 359, 367, 428/360; 501/95; 210/510.1, 505, 496, 509, 508, 777

[56] References Cited

U.S. PATENT DOCUMENTS

| | | | |
|---|---|---|---|
| 3,974,072 | 8/1974 | Birchall et al. | 501/95 |
| 3,996,145 | 12/1976 | Hepburn | 501/95 |
| 4,116,761 | 9/1978 | Head | 210/509 |
| 4,177,142 | 12/1979 | Halbfoster | 210/505 |
| 4,238,334 | 12/1980 | Halbfoster | 210/505 |
| 4,313,832 | 2/1982 | Shimizu et al. | 210/505 |
| 4,560,478 | 12/1985 | Narumiga | 210/510.1 |
| 4,576,716 | 3/1986 | Ida et al. | 210/505 |
| 4,594,158 | 6/1986 | Chong et al. | 210/505 |
| 4,698,157 | 10/1987 | Gillot | 210/510.1 |
| 4,789,479 | 12/1988 | Onitsuka et al. | 210/505 |
| 5,030,611 | 7/1991 | Ogawa et al. | 210/503 |

OTHER PUBLICATIONS

Saffil Fibers-New Media For High Performance Liquid (Translation) Filtration; Chemical Engineering, Jun., 1977, pp. 526-531.
Chemical Engineering, Jun. 1988, pp. 526-531. Translation of p. 526 left column, lines 1-20.
Kagaku Sochi, Mar. 1983, pp. 39-51. Translation of p. 39, left col., line 15 thru p. 39, right col., line 3.
Hyomen, vol. 19, No. 3, pp. 123-133, 1981. Translation of p. 124, right col., line 2 thru p. 125, left col., line 8.

Primary Examiner—Patrick J. Ryan
Assistant Examiner—J. M. Gray
Attorney, Agent, or Firm—Browdy and Neimark

[57] ABSTRACT

The present invention relates to a filter aid for analytical use and method for preparing the same, more particularly, a filter aid for analytical use consisting essentially of tangled short-length ceramic fibers having a bulk density in the range of about 0.02–0.18 g/cm$^3$ and method for preparing the same.

10 Claims, 3 Drawing Sheets

FILTER AID FOR ANALYTICAL USE AND METHOD FOR PREPARING THE SAME

This application is a continuation of application Ser. No. 07/248,282 filed Sep. 22, 1988, now abandoned.

BACKGROUND OF THE INVENTION

1. Field of the Invention

The present invention relates to a filter aid for analytical use and method for preparing the same, more particularly, a filter aid for analytical use consisting essentially of tangled short-length ceramic fibers having a bulk density in the range of about 0.02–0.18 g/cm$^3$ and method for preparing the same.

2. Description of the Prior art

Quantification of crude fibers in the component analysis of foods and feeds has a significance in evaluating their nutritional components, as well as in evaluating unassimilable or scarcely assimilable components such as dietary fibers.

Conventionally, quantitative analysis of crude fibers is carried out as follows: A sample which has been accurately weighed is boiled in 1.25% aqueous sulfuric acid solution. The mixture is filtered and washed while it is hot. The residue was boiled together with a filter aid in 1.25% aqueous sodium hydroxide solution, and the resultant is filtered and washed while it is hot. The residue is dried together with a filter bed formed by the filter aid to give a constant weight. They are then incinerated to determine the loss, followed by calculating its percentage against the weight of the sample.

Usually, asbestos has been used as a filter aid.

Recently, it is found that asbestos is one of the substances which are responsible for the occurrence of lung cancer, and the replacement of the asbestos with ceramic fiber has been proposed (*Chemical Engineering*, Issue of June, pp. 526–531, 1977, and *Kagaku Sochi*, Issue of March, pp. 39–51, 1983).

Since a filter aid for analytical use of ceramic fiber has not been commercialized, analysts in the field have been expecting the development of such filter aid.

SUMMARY OF THE INVENTION

Since a filter aid for analytical use of ceramic fiber has been scarcely studied, we studied the conditions and physicochemical features which should to have. We continued studying the conditions and features in order to establish a filter aid for analytical use consisting essentially of ceramic fibers and a method for preparing the same.

As a result, it was found that the important factors of ceramic fibers for use in quantitative analysis of crude fibers, for example, those in foods and feeds were as follows: Acid-, alkaline-, and thermal-resistances: handleability in weighing a predetermined amount; easiness in the formation of a filter bed; filterability; and retainability of a filter bed when it was moved after it had been used in filtration, particularly, retainability of a filter aid together with a residue after they had been subjected to incineration. Furthermore, we found that a filter aid for analytical use consisting essentially of tangled short-length ceramic fibers having a bulk density in the range of about 0.02–0.18 g/cm$^3$ was favorably used.

BRIEF DESCRIPTION OF THE ACCOMPANYING PHOTOGRAPHS

DETAILED DESCRIPTION OF THE INVENTION

Figure 1:
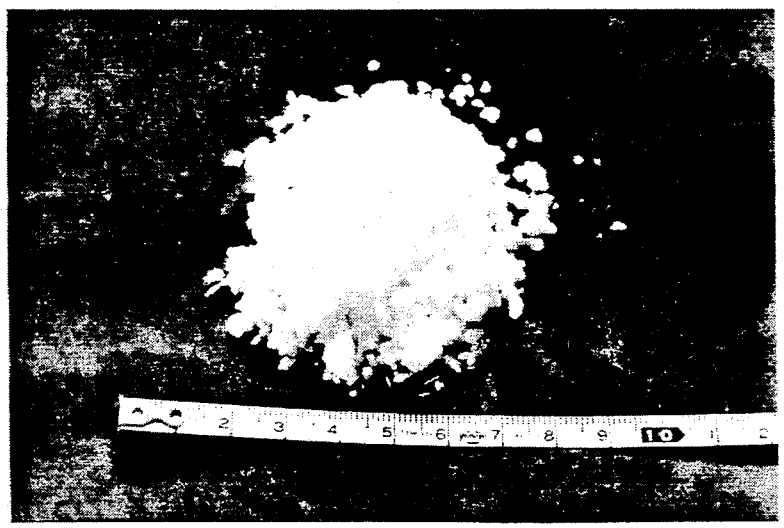
FIG. 1 is the exterior view of a filter aid for analytical use consisting essentially of tangled short-length ceramic fibers having a bulk density of about 0.05 g/cm$^3$.

The present invention relates to a filter aid for analytical use consisting essentially of tangled short-length ceramic fibers having a bulk density in the range of about 0.02–0.18 g/cm$^3$, preferably, a filter aid for analytical use consisting essentially of small masses of tangled short-length ceramic fibers.

Such filter aid is prepared by the following method: Commercialized long-length ceramic fibers such as aluminum-silica fiber and aluminum fiber are cut, for example with a mixer in water, and the resultant is mixed to obtain a short-length ceramic fiber, about 3 mm or shorter in length. Then, the resultant mixture is washed and dehydrated by the method such as filtration and centrifugation to obtain a mass such as a residue or a precipitate which is made of tangled short-length ceramic fibers. The mass is unraveled to form a small mass, about 1–10 mm in diameter, and which is then subjected to drying or drying by heating until it shows a constant weight to obtain a filter aid for analytical use consisting essentially of tangled short-length ceramic fibers having a bulk density in the range of about 0.02–0.18 g/cm$^3$ and a length of about 3 mm or shorter, preferably, a length of 0.01–2 mm.

The warding "short-length ceramic fibers" as referred to in the present invention includes ceramic fibers, for example, those described in "Hyomen", Vol. 19, No. 3, pp. 123–133 (1981) which are excellent in acid-, alkaline- and thermal-resistances without fear of causing lung cancer. For example, alumina-silica fiber, alumina fiber, slag rock fiber, potassium titanate fiber and zirconia fiber can be favorably used as the short-length ceramic fiber. Furthermore, the short-length ceramic fiber includes those which can be prepared by cutting a ceramic fiber such as aluminum-silica fiber and aluminum fiber, about 2–4 μm in diameter, about 30–250 mm or longer in length, into about 3 mm or shorter pieces, preferably, about 0.01–2 mm pieces.

Since short-length ceramic fibers when they are dried may be scattered by a static electricity and a gentle wind, they are attached to skins or mucous membranes to cause stimulant reaction therein. Therefore, the ceramic fibers should be cut under humid conditions, preferably, in water.

To tangle the short-length ceramic fibers according to the present invention is essential in order to prevent scattering and falling caused by a static electricity and a gentle wind when the fibers are weighed, and to form small masses which can improve handleability, as well as to facilitate analysis and to improve analytical accuracy while retaining a bulk density of a filter aid for analytical use in the range of about 0.02–0.18 g/cm³.

The method for tangling those short-length ceramic fibers is as follows: For example, long-length ceramic fibers are cut in water, and the resultant is mixed. The mixture is then dehydrated by an appropriate method such as filtration and centrifugation to form masses such as those of a residue and a precipitate, followed by collecting the masses.

Furthermore, the masses are tangled to form regularly or irregularly shaped small masses, about 1–10 mm in diameter, and which are then subjected to drying or drying by heating until they show a constant weight to obtain a filter aid for analytical use consisting essentially of small masses of tangled short-length ceramic fibers having a bulk density in the range of about 0.02–0.18 g/cm³. In a method of drying, for example, through-flow drying and drying by heating can be favorably used. When using the filter aid for analytical use in quantitative analysis of crude fibers in foods, drying by heating at the same or a higher temperature as used in incineration, for example, incineration at a temperature in the range of about 400–800° C. for about 2–20 hours can be favorably used in order to preeliminate the ignition loss from the filter aid. When a filter aid for analytical use is treated with acid or alkaline, the filter aid for analytical use can be favorably pretreated therewith to prepare a filter aid for analytical use, if necessary.

The filter aid for analytical use consisting essentially of tangled short-length ceramic fibers having a bulk density in the range of about 0.02–0.18 g/cm³ is excellent in acid-, alkaline-, and thermal-resistances. Furthermore, the filter aid possesses requirements of a filter aid for analytical use, for example, handleability in weighing a predetermined amount, easiness in the formation of a filter bed, filterability, and retainability of a filter bed after it has been used in filtration.

The filter aid for analytical use according to the present invention is favorably used in a quantitative analysis for crude fibers, for example, those in foods and feeds. Furthermore, it is favorably used in a quantitative analysis for reducing sugars, for example, those in foods and partial starch hydrolysates by the Bertrant method.

The weight of the filter aid for analytical use according to the present invention is extremely cut when it is used in an analysis because its bulk density is about ⅕–1/5 of that of asbestos.

The following Experiments will explain the filter aid for analytical use according to the present invention in detail.

under the Trademark of "SAFFIL ®", bulk density of about 0.005 g/cm³, about 3 μm in diameter and about 30–60 mm in length, was cut and mixed with a mixer for about 5 seconds in the presence of 200 parts by weight of water, and the resultant mixture was separated into upper, middle and lower beds by a brief standing. These beds were separately filtered, washed and dehydrated. Then, the resultant masses were collected, unraveled by an unraveling machine to prepare small masses, about 1–6 mm in diameter each. The resultants were then separately incinerated at 600° C. for 16 hours to obtain filter aids for analytical use having a bulk density of about 0.02, 0 05 and 0.18 g/cm³. Another cottony ceramic fiber was cut with a mixer for about 60 seconds in the presence of water. The resultant was mixed and allowed to stand for a while. Then, the lower bed of the mixture was collected, filtered, and dehydrated. The obtained product was unraveled into small masses, and which were then incinerated to obtain a filter aid for analytical use having a bulk density of about 0.40 g/cm³.

Those ceramic fibers varying in their bulk densities were compared with conventional asbestos for Gooch crucible with respect to the following items (1) through (5) which were required in a filter aid for analytical use:

(1) Handleability in weighing ceramic fibers with spoon.

(2) Easiness in the formation of a filter bed on a glass-fiber filter, 47 mm in diameter, 0.6 μm in average pore size, which is formed by vacuum filtration of 1 g ceramic fibers. In the case of using asbestos for Gooch crucible, 3 g of the asbestos is used in relation to its bulk density.

(3) Filterability of a sample solution obtained by boiling down 5 g "nama-an (bean jam not yet sweetened with sugar)" in 200 ml of 1.25% aqueous sulfuric acid solution for 30 minutes by using a filter bed prepared by the method in item (2).

(4) Retainability of a filter bed when it is detached from a glass-fiber filter having been used in filtration by the method in item (3).

(5) Retainability of a filter bed which has been detached from a glass-fiber filter by the method in item (4) and subjected to 1-hour incineration at 500° C.

The evaluation was graded into 3 groups, i.e. "superior" meaning a filter aid which is advantageously usable to asbestos, "passable" meaning one which is equally usable to asbestos, and "unpassable" meaning one which is inferior to asbestos and unusable as a filter aid for analytical use.

The results were as shown in Table.

TABLE

| Bulk density (g/cm³) | 1 Handleability in weighing | 2 Easiness in formation of filter bed | 3 Filterability | 4 Retainability of filter bed after filtration | 5 Retainability of filter bed after incineration | Appreciation |
| --- | --- | --- | --- | --- | --- | --- |
| 0.005 | Unpassable | Unpassable | Unpassable | Unpassable | Unpassable | Control |
| 0.02 | Passable | Passable | Superior | Passable | Passable | Present invention |
| 0.05 | Superior | Superior | Superior | Passable | Passable | Present invention |
| 0.18 | Passable | Superior | Superior | Passable | Passable | Present invention |
| 0.40 | Unpassable | Superior | Passable | Unpassable | Unpassable | Control |

Experimental items Number

EXPERIMENT

Relationship Between Bulk Density of Ceramic Fibers and Filter Aid for Analytical Use One part by weight of a cottony ceramic fiber, commercialized by Isolite Insulating Products Co., Ltd., As evident from the results in Table, it was found that the filter aid for analytical use according to the present invention consisting essentially of tangled short-length ceramic fibers having a bulk density in the range of about 0.02-0.18 g/cm³ favorably satisfied the requirements of a filter aid for analytical use, particularly, the filter aid for analytical use according to the present invention was excellent in filterability because it can extremely reduce the filtration period than in the case of using asbestos.

It was found that the filter aid having a bulk density of lower than about 0.02 g/cm³ which is usually composed of ceramic fibers, longer than about 3 mm in length, could not be used as a filter aid for analytical use wherein accuracy was required because of the following reasons: The filter aid was too bulky to weigh: the formation of a filter bed by the filter aid was unfavorable; the filter aid was readily clogged by a sample which had been passed through it: and the filter bed was swelled to about 2-5 volumes after it had been incinerated, and it was then easily damaged and degraded when it was moved and weighed.

It was found that the filter aid having a bulk density higher than about 0.18 g/cm³ which was usually composed of microscopic particles of ceramic fibers, shorter than about 0.001 mm in length, could not be used as a filter aid for analytical use similarly as the product having a bulk density lower than about 0.02 g/cm³ because of the following reasons: The filter aid was scarcely tangled and easily scattered and fallen down by a static electricity and a gentle wind; the filter aid was easily clogged when it was used in filtration; and a filter bed formed by the filter aid was easily damaged and degraded by a slight shock when it was moved and weighed.

Figure 2:
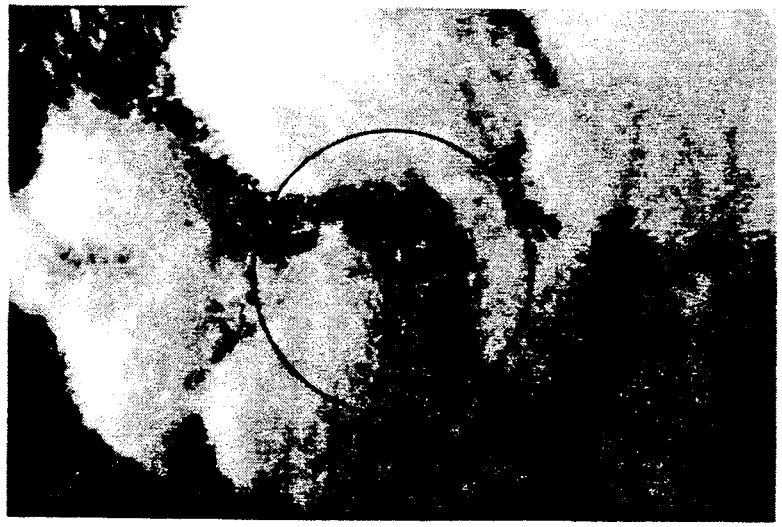
FIG. 2 is the partial enlarged figure of the product in FIG. 1.
Figure 3:
FIG. 3 is the exterior view of a filter bed formed by the product in FIG. 1.
Figure 5:
FIG. 5 is the partial enlarged figure of the product in FIG. 4.
Figure 6:
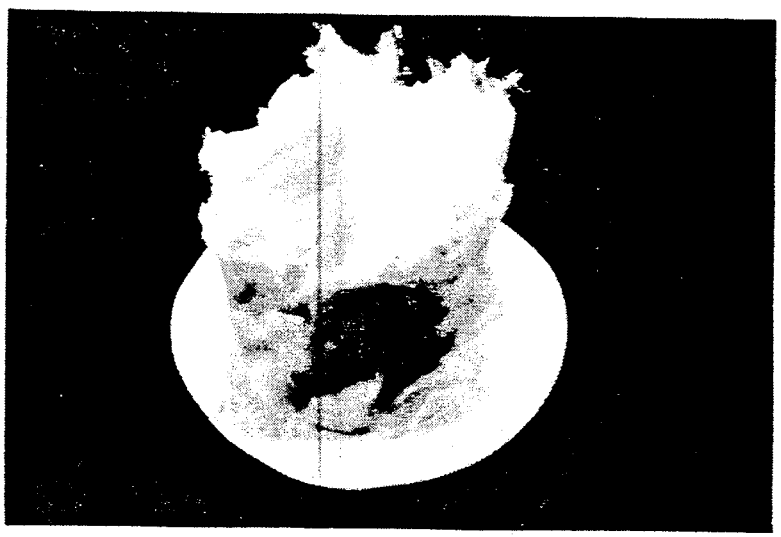
FIG. 6 is the exterior view of a filter bed formed by the product in FIG. 4.

As for a reference, FIG. 1 is the exterior view of a filter aid for analytical use consisting essentially of tangled short-length ceramic fibers having a bulk density of about 0.05 g/cm³, FIG. 2 is the enlarged figure thereof, and FIG. 3 is the exterior view of a filter bed formed thereby. As control, for example, FIG. 4 is the exterior view of a cottony filter aid for analytical use having a bulk density of about 0.005 g/cm³ which is composed of long-length ceramic fibers, FIG. 5 is the enlarged figure thereof, and FIG. 6 is the exterior view of a filter bed formed thereby.

Figure 4:
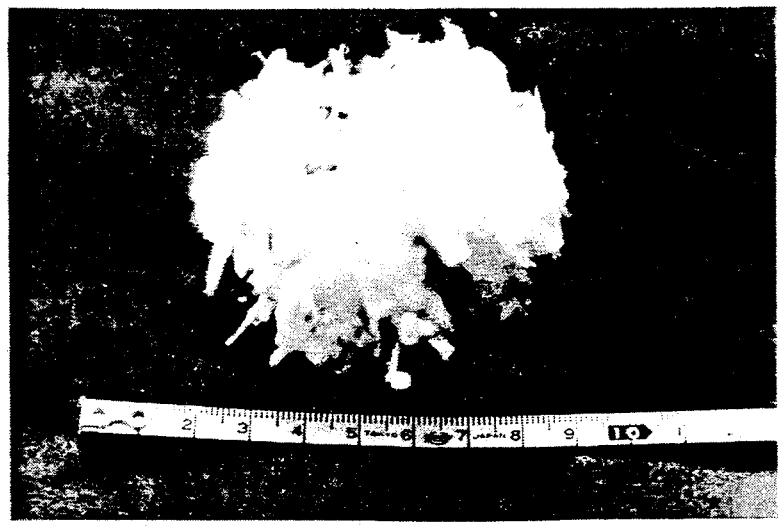
FIG. 4 is the exterior view of a cottony product composed of long-length ceramic fibers having a bulk density of about 0.005 g/cm$^3$.

In FIGS. 1 and 4, the minimum scale is 1 mm. In FIGS. 3 and 6, the filter papers are 47 mm in diameter.

As evident from the figures, the filter aid for analytical use according to the present invention consisting essentially of small masses can form a regularly arranged filter bed.

Several Examples according to the present invention will hereinafter be explained.

EXAMPLE 1
Filter Aid for Analytical Use

One part by weight of a cottony ceramic fiber, commercialized by Isolite Insulating Products Co., Ltd., under the Trademark of "SAFFIL ®", was cut with a mixer for about 10 seconds in the presence of 50 parts by weight of water. The resultant was mixed, filtered, washed and dehydrated. The residue was then fed to an unraveling machine to obtain small masses, about 1-4 mm in diameter. The small masses were incinerated at 700° C. for 5 hours to obtain a filter aid for analytical use consisting essentially of small masses of tangled short-length ceramic fibers having a bulk density of about 0.07 g/cm³ in the yield of about 95% by weight.

The product favorably satisfies the requirements of a filter aid for analytical use, and it is advantageously used in quantitative analysis for crude fibers, for example, those in foods and feeds. Furthermore, the product is advantageously used in quantitative analysis for reducing sugars, for example, those in partial starch hydrolysates by the Bertrant method.

EXAMPLE 2
Filter Aid For Analytical Use

One part by weight of a cottony ceramic fiber, commercialized by Isolite Insulating Products Co., Ltd., under the Trade Name of "KAOWOOL" was cut with a mixer for about 5 seconds in the presence of 70 parts by weight of water. The resultant was mixed, filtered, washed and dehydrated. The residue was then fed to an unraveling machine to obtain small masses, 1-6 mm in diameter. The small masses were incinerated at 600° C. for 12 hours to obtain a filter aid for analytical use consisting essentially of tangled small masses of short-length ceramic fibers having a bulk density of about 0.04 g/cm³ in the yield of about 90% by weight.

The product favorably satisfies the requirements of a filter aid for analytical use, and it is favorably used as such filter aid similarly as the product in Example 1.

EXAMPLE FOR REFERENCE
Quantitative Analysis of Crude Fiber

A half gram of bran which had been accurately weighed was placed in a 500-ml Erlenmeyer flask, and added with 0.5 g of a filter aid for analytical use prepared by the method in Example 1. The mixture was added with 200 ml of 1.25% aqueous sulfuric acid solution which had been preboiled. Then, a reflux condenser was set to the Erlenmeyer flask, and the resultant mixture was refluxed for 30 minutes. The reaction mixture was poured onto a glass-fiber filter, 47 mm in diameter, 0.6 μm in average pore size, and the residue was sufficiently washed with hot water until the filtrate did not show acidity.

The residue was washed together with the filter bed into another 500-ml Erlenmeyer flask with 200 ml of 1.25% aqueous sodium hydroxide solution which had been preboiled, and a reflux condenser was set to the Erlenmeyer flask in order to reflux the mixture solution for 30 minutes. The resultant mixture was subjected to vacuum filtration with a filter bed which had been prepared by using about 1 g of a filter aid for analytical use prepared by the method in Example 1. The residue was sufficiently washed with hot water until the filtrate did not show alkalinity while removing the filtrate.

Thereafter, the filter bed was washed 3-times with 5 ml aliquots of ethyl alcohol, and the residue was dehydrated.

The residue was detached together with the filter bed from the glass-fiber filter, and they were placed into an aluminum vessel to determine their constant weight, and dried at 105° C. until they showed a constant weight ("A" g by weight). The dry substance ("A" g by weight) was placed in an electric oven, and allowed it to stand at 500° C. until it showed a constant weight ("B" g by weight). The crude fiber content in the bran was determined by the following formula:

$$\text{Crude fiber content (\%)} = \frac{A (g) - B (g)}{\text{Weight of bran (g)}} \times 100$$

By using about 2-volumes of conventional asbestos for Gooch crucible in place of the present filter aid, quantitative analysis for crude fiber in a fresh preparation of the same bran as used in the above was similarly determined.

In each case, crude fiber content of bran was 7.7%.

It was found that the present filter aid could be used in the field in place of conventional asbestos for Gooch crucible.

EFFECT OF THE INVENTION

As evident from the above, the filter aid for analytical use according to the present invention consisting essentially of tangled short-length ceramic fibers having a bulk density in the range of about 0.02–0.18 g/cm$^3$, preferably, the filter aid essentially consisting of small masses of tangled short-length ceramic fibers is excellent in acid-, alkaline- and thermal-resistances, as well as in handleability in weighing a predetermined amount thereof, easiness in the formation of a filter bed, filterability, and retainability of a filter bed after it has been used in filtration and incineration. Since the present filter aid is excellent in filterability as compared with the case of using asbestos, it can extremely reduce the filtration time.

The filter aid can be favorably used as a filter aid for analytical use in quantitative analysis for crude fibers, for example, those in foods and feeds. Furthermore, the filter aid can be favorably used in quantitative analysis for reducing sugars, for example, those in foods and partial starch hydrolysates by the Bertrant method. The weight of the filter aid for analytical use according to the present invention is extremely cut in an analysis because its bulk density is about ½–1/5 of that of asbestos.

Furthermore, the filter aid for analytical use according to the present invention effectively diminishes anxiety of analysts who have been using conventional asbestos filter aid because the present filter aid does not have fear of causing lung cancer.

We claim:

1. A filter aid for quantitative analysis of reducing sugars and crude fibers in foods and feeds, consisting essentially of small masses of tangled short-length ceramic fibers having a bulk density in the range of about 0.02–0.18 g/cm$^3$ and a length of 0.001–3 mm, said small masses each being about 1–10 mm in diameter and having been dried at an elevated temperature of at least about 400–800° C. for about 2–20 hours.

2. A filter aid according to claim 1, wherein said ceramic fibers are selected from the group consisting of alumina/silica fibers, alumina fibers, slag rock fibers, potassium titantate fibers, zirconia fibers and mixtures thereof.

3. A filter aid according to claim 2, wherein said fibers have diameters of about 2–4 μm.

4. A filter aid according to claim 1, which has been treated with acid.

5. A filter aid according to claim 1, which has been treated with alkaline.

6. A filter aid for quantitative analysis of reducing sugars and crude fibers in foods and feeds, consisting essentially of small masses of tangled short-length ceramic fibers having a bulk density in the range of about 0.02–0.18 g/cm$^3$ and a length of 0.001–3 mm, said small masses each being about 1–10 mm in diameter and being capable of being incinerated without destruction.

7. In a method for the quantitative analysis of edible fibers and reducing sugars comprising filtering a liquid sample of a food product through a filter together with a filter aid, the improvement wherein said filter aid is the filter aid of claim 1.

8. A method according to claim 7, wherein said ceramic fibers of said filter aid are selected from the group consisting of alumina/silica fibers, alumina fibers, slag rock fibers, potassium titanate fibers, zirconia fibers and mixtures thereof.

9. A method according to claim 7, wherein said ceramic fibers of said filter aid have diameters of about 2–4 μm.

10. A method according to claim 7, wherein said ceramic fibers of said filter aid have been treated with acid.

* * * * *